United States Patent [19]

Dunseath, Jr.

[11] Patent Number: 5,003,978

[45] Date of Patent: Apr. 2, 1991

[54] NON-POLARIZABLE DRY BIOMEDICAL ELECTRODE

[75] Inventor: W. J. Dunseath, Jr., Durham, N.C.

[73] Assignee: Technology 21, Inc., Durham, N.C.

[21] Appl. No.: 403,825

[22] Filed: Sep. 7, 1989

Related U.S. Application Data

[63] Continuation-in-part of Ser. No. 196,661, May 20, 1988, Pat. No. 4,865,039, which is a continuation of Ser. No. 989,235, Aug. 20, 1986, which is a continuation-in-part of Ser. No. 767,963, Aug. 25, 1985.

[51] Int. Cl.[5] .............................................. A61B 5/402
[52] U.S. Cl. ..................................................... 128/640
[58] Field of Search ............................... 128/639–641, 128/644, 798, 802, 807

[56]  References Cited

U.S. PATENT DOCUMENTS 3,993,049  11/1976  Kater ..................................... 128/640
4,352,359  10/1982  Larimore et al. .................... 128/640
4,458,696  7/1984  Larimore ............................. 128/640
4,727,881  3/1988  Craighead et al. ................. 128/641
4,852,571  8/1989  Gadsby et al. ....................... 128/640

Primary Examiner—Lee S. Cohen
Attorney, Agent, or Firm—Oblon, Spivak, McClelland, Maier & Neustadt

[57] ABSTRACT

A dry electrode for the detection of biopotentials existing on the surface of the skin of a living body, including a non-polarizable dry electrode pad having opposed adhesive surfaces, one of which is adapted to engage the skin of the living body and extend ionic charge conduction from the body to the surface of a non-polarizable electrode interface within the pad. An electrically conductive contact makes electrical and mechanical connection from the electrode pad to a wire or electronic amplifier by means of a second adhesive surface on the electrode pad. In a preferred embodiment, conductive adhesive layers are applied to opposed sides of a conductive foam pad to construct the dry electrode pad.

36 Claims, 1 Drawing Sheet

NON-POLARIZABLE DRY BIOMEDICAL ELECTRODE

CROSS REFERENCE TO RELATED APPLICATIONS

This application is a continuation-in-part of U.S. application Ser. No. 07/196,661 filed May 20, 1988, which issued as U.S. Pat. No. 4,865,039, which was a continuation of U.S. application Ser. No. 06/898,235 filed Aug. 20, 1986, which issued as U.S. Pat. No. 4,763,659, which was a continuation-in-part of U.S. application Ser. No. 06/767,963 filed Aug. 25, 1985, which issued as U.S. Pat. No. 4,669,4779.

BACKGROUND OF THE INVENTION

1. Field of the Invention

The invention described herein pertains to the detection of potentials existing on the surface of the skin of the living body, which potentials are generated by various sources such as muscle or nervous system activity within the body.

2. Discussion of the Background

Present biopotential detection techniques typically involve the use of conductive pastes or gels in combination with a metallic contact surface to form an electrode capable of transforming electrical charge conduction by means of ion diffusion in the body into electrical charge conduction by means of electron motion in the metallic wires of the monitoring apparatus. There are several realizations of this basic type of electrode, and all of them suffer from the various disadvantages of wet systems, such as skin irritation, loss of electrical contact due to drying paste or lead wires falling off, poor shelf life, etc. Many electrodes for use in electrocardiography are designed to withstand high voltage overloads, such as encountered during a defibrillation procedure, by rapid recovery to the original electrode potential. Such performance is required in operating rooms or critical care areas where it is important to maintain constant monitoring of the activity of the heart, and electrodes exhibiting this quality are usually called non-polarizing or reversable. Virtually all of the reversable electrodes currently available utilize an electrolyte gel that is subject to drying, thus suffering from the limitations of wet systems as listed above. Various materials have been introduced in attempts to realize dry electrodes, but none of them have been successful in providing a high performance, non-polarizable dry electrode.

For example, most of the metals and conductive composite materials introduced in the prior art as dry electrodes, such as those disclosed in U.S. Pat. Nos. 3,566,860 and 3,606,881, generate excessive low frequency electrical noise voltages when in contact with a saline solution such as human sweat or blood. Furthermore, many of these materials are too stiff to conform to irregularities in skin surface, thus resulting in an uncomfortable and electrically unstable electrode. Another effort to obtain dry electrodes includes conventional non-conductive pressure sensitive adhesives loaded with fine conductive particles such as carbon power (U.S. Pat. No. 3,911,906) or metal-coated plastic microspheres (U.S. Pat. No. 3,566,059). However, such electrodes suffer from low electrical conductivity to skin resulting in poor signal quality. Furthermore, a method for making such adhesives reversable has not been demonstrated.

In my U.S. Pat. Nos. 4,751,471 and 4,763,659, a dry electrode that is stable in the presence of saline, conformable to body contours, and capable of delivering a high quality signal to any suitable measuring apparatus despite wide ranges in electrode impedance to skin is disclosed. Although this electrode is acceptable for procedures such as diagnostic electrocardiography, a means for making the electrode non-polarizable in the presence of saline body fluids has not been disclosed.

Materials having both adhesive and electrically conductive properties have been introduced for use as dry electrodes, such as disclosed in U.S. Pat. No. 4,273,135. Although it is stated that such materials are suitable for use in defibrillation procedures, they still suffer from limitations in adhesion and require an extra adhesive patch to hold the electrode in place. Again, there is no provision for protecting the electrode from polarization when subject to defibrillation overloads in the presence of saline body fluids. The materials specified for use as connectors all form polarizable electrode interfaces when in contact with ionically conductive solutions such as saline, which could flood through or around the thin (25 to 100 microns) layers of conductive film stipulated for this electrode. A similar problem exists with the electrode construction described in U.S. Pat. No. 4,458,696 and G.B. Patent 2,045,088. The carbon-loaded polymeric connectors as specified form polarizable electrode interfaces when in contact with saline solutions, but the thin layers of adhesive of this electrode do not provide an adequate fluid barrier. An electrode polarization problem also exists with the construction disclosed in U.S. Pat. No. 4,125,110, which shows a thick layer of karaya based adhesive loaded with sodium chloride to obtain ionic conductivity. The electrically conductive backing is obtained from wire mesh, conductive cloth or conductive polymer materials, any of which are polarizable when in contact with dissolved sodium chloride.

Kater (U.S. Pat. No. 3,993,049) discloses a method for realizing a non-polarizable electrode by loading a metal salt into an adhesive and making a backing connector of the metal of the metal salt in the adhesive. Various complicated structures are described, including the use of metal screens and connectors incorporated into the electrode, all of which are difficult to manufacture and not extensible with skin. In addition, the presence of metal salts in material touching the skin increases the risk of skin irritation, and the preferred mode of including metal salts and powders in an adhesive not only increases the risk of skin irritation but further reduces the tack of the adhesive. Other non-polarizable electrodes disclosed in the prior art involve the use of gels with a high water content, as in U.S. Pat. No. 4,235,241, which discloses a non-polarizing backing plate consisting mainly of titanium hydride and silver chloride. Electrical contact to the skin is achieved through an electroconductive cream impregnated with sodium chloride, which is subject to drying out while the electrode may still be in use. The most common reversible electrode is based on a silver connector having a layer of silver chloride deposited on its surface, combined with an electrolyte gel of high water content containing dissolved chloride ions. This is known as the silver/silver chloride electrode, and it has been disclosed in various patents including U.S. Pat. No. 4,377,170. As with Kater above, the basic principle involved in realizing a non-polarizable electrode interface is to combine certain metals and their respective salts within the electrode to enable the exchange of electrons and ions to proceed freely at the interface between the electrode and electrolyte solution, thus allowing large rapid potential changes across the electrode interface without residual polarization. However, no method for realizing such a non-polarizable electrode that is dry, body conformable, adhesive and non-irritating to skin, in the presence of substantial amounts of body fluids such as blood or saline, has heretofore been disclosed.

SUMMARY OF THE INVENTION

Accordingly, it is an object of the present invention to provide a new and improved dry electrode and electrode system for detecting potentials on the skin of a living body without the use of conductive pastes or gels under conditions ranging from dry to sweat-soaked skin.

A further object of this invention is to provide a novel dry electrode and electrode system which in the presence of body fluids such as sweat or blood remains stable and non-polarizable after exposure to repeated defibrillation overload voltages and other voltages or currents as may arise in the medical environment.

Yet another object of this invention is to provide a novel dry electrode system capable of providing a signal to conventional monitoring devices without the need for adjustment or modification to the monitor.

These and other objects are achieved according to the invention by providing a novel dry electrode pad formed of a conductive substrate containing a metal salt or other material for forming a non-polarizable electrode interface at the surface of or throughout the conductive substrate, a first adhesive layer for adhering the dry electrode pad to the skin and extending the ionic conductivity of the body to the conductive substrate and a second adhesive layer for adhering a conductive contact, also comprised of nonpolarizable material, to the opposite side of the pad. The conductive contact is connected to the input of a lead amplifier such as disclosed in my U.S. Pat. No. 4,763,659, or directly to a wire.

According to one embodiment of the invention, the conductive substrate is coated on one side with an adhesive containing dissolved chloride ions and adapted to adhere to the skin, and the opposite side of the conductive substrate is coated, except for the central portion, with a non-conductive adhesive for adhering the conductive contact to the electrode pad.

In a preferred embodiment, one side of the conductive substrate is coated with an adhesive containing dissolved chloride ions and adapted to adhere to the skin, and the opposite side of the conductive substrate is coated with a conductive adhesive comprised of non-polarizing material as in the conductive substrate and adapted to adhere to the conductive contact.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1A:
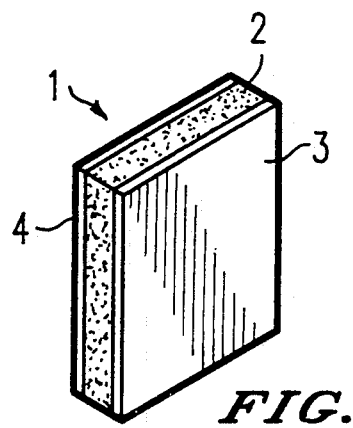
FIGURES 1a and 1b are perspective views of opposite sides of one embodiment of the dry electrode pad with a conductive substrate according to the invention.
Figure 1B:
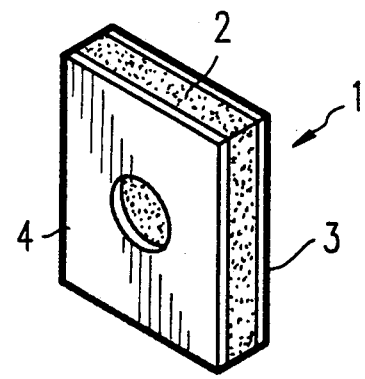
Figure 1C:
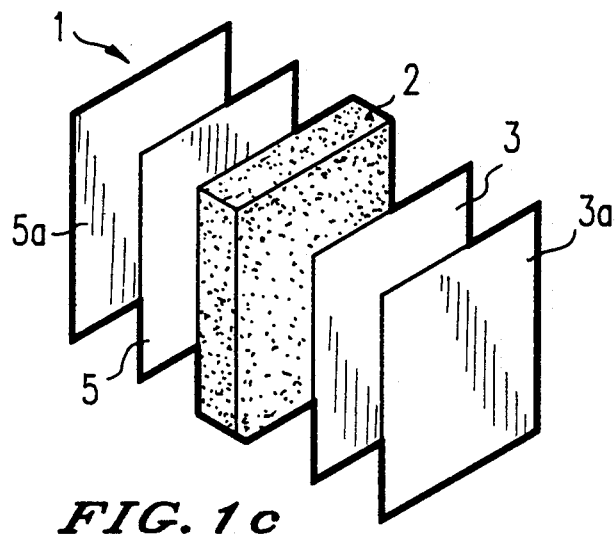
FIGS. 1c and 1d are perspective view of a preferred embodiment of the dry electrode pad of the invention.

Referring now to the drawings, wherein like reference numerals designate identical or corresponding parts throughout the several views, and more particularly to FIGURES 1a–1c thereof, an embodiment of the dry electrode pad 1 of the present invention is shown. As shown in FIGS. 1a and 1b, the dry electrode pad 1 of the invention includes a conductive substrate 2 coated with a conductive adhesive 3. The conductive substrate 2 is a material with two essential traits: electrical conductivity and electrical stability. The electrical conductivity of conductive substrate 2 must be sufficient to establish a 10 Hz impedance of 5 kilohms (k$\Omega$) or less to a saline solution containing 1.5% by weight dissolved sodium chloride. Similarly, the electrical stability of conductive substrate 2 in contact with a 1.5% saline solution is sufficient to meet the requirements outlined in the DC Offset Voltage, Combined Offset Instability and Internal Noise, Defibrillation Overload Recovery, and Bias Current Tolerance requirements of the American National Standard for Pregelled ECG Disposable Electrodes (ANSI/AAMI EC-12 1983). In particular, the conductive substrate 2 in contact with a 1.5% saline solution must exhibit an offset voltage of less than 100 millivolts (mV), generate AC noise voltages no greater than 150 ($\mu$V) in the passband of 0.15 to 100 Hz, exhibit polarization potentials not exceeding 100 mV after four defibrillation pulses of 2 millicoulombs charge at 200 volts potential, and tolerate a continuous 200 nanoampere (nA) current for greater than 8 hours without a DC offset voltage change exceeding 100 mV, all of the above measurements being made across the interface of conductive substrate 2 and the 1.5% saline solution.

In addition, if electrode pad 1 is to be larger than approximately 0.25 square inches, such as for use in electrocardiography, it is desirable that conductive substrate 2 be composed of a material exhibiting resiliency. Thus the material must be flexible in order to conform to body surface contours yet possess a sufficient resiliency to maintain intimate contact with the skin despite dynamic variations in contour, for example due to breathing or similar bodily movement. In this case, the resiliency of the material forming conductive substrate 2 as measured by the Ball Rebound Test (ASTM Designation D 3574-81) must exceed 5% and preferably be as high as 20%.

Since conductive adhesive 3 isolates the surface of conductive substrate 2 from direct contact with the skin of the body, a wide range of materials may be used as components of conductive substrate 2 without the risk of skin irritation. For example, a mixture of very finely ground silver and silver chloride powders may be loaded into polymeric materials such as silicone rubber, plasticized polyvinyl chloride, polyurethane foam, polytetrafluoroethylene (TEFLON TM) or other similar materials that presently are commonly rendered conductive by carbon impregnation. Other combinations of fine powders of metals and their salts, such as zinc and zinc sulfate, may also be used as loading components of conductive substrate 2 within the restriction that a non-polarizable electrode interface be established within conductive substrate 2 as a result. Other materials that are known to form reversible junctions when in contact with physiological saline solutions, such as titanium hydride, or mixtures of titanium hydride, silver chloride, sodium tungstate dihydrate and graphite, as disclosed in U.S. Pat. No. 4,235,241, may also be used as loading materials for conductive substrate 2.

Figure 1D:
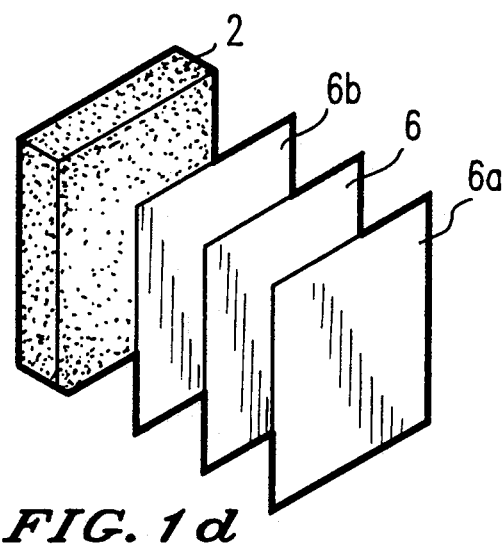

Conductive adhesive 3 serves to hold electrode pad 1 in both mechanical and electrical contact with the skin, and is a pressure sensitive hypo-allergenic medical adhesive providing a tacky skin-engaging surface. In addition, adhesive 3 serves as an extension of the electrical conductivity of the body by the diffusion of chloride ions through the adhesive, in the same concentration by weight as is found in human sweat, approximately 0.15% to 1.5%. Thus sodium chloride, or alternatively, potassium chloride, dissolved in small quantities in a water-based adhesive serves to extend the ionic charge conduction of the body to the electrode interface found in conductive substrate 2. The amount of water in the adhesive, approximately 5% by weight, is low enough to preclude the drying out of the electrode during use, while the concentration of electrolyte, being similar to that found in physiological salines, is low enough to avoid irritating skin or reducing the tack of the adhesive. As shown in FIG. 1d, a tissue carrier 6 coated on both sides with conductive adhesives 6a and 6b meeting the requirements given above for conductive adhesive 3 may be used as a manufacturing aid when laminating adhesives to conductive substrates having rough or celled surfaces, such as foamed material. In addition, a second layer of adhesive that is insoluble in water may be coated on a portion of the exterior surface of adhesive layer 3, or on layer 6a to maintain strong adhesive tack to wet skin over long periods of time. The second adhesive is a non-conductive medical adhesive as is typically used in medical electrodes; Type MA-23 adhesive manufactured by Adhesives Research, Inc., Glen Rock, Pa. is an acceptable example.

Several adhesives meeting the above listed specifications for conductive adhesive 3 are known and their selection is well within the skill of the adhesive technologist. Suitable adhesive bases include, but are not limited to, polyvinylpyrrolidone, polyvinylpyridines, vinyl ether polymers and cellulose derivatives. For example, an ionically conductive adhesive can be formed by mixing equal parts of a vinyl ether polymer such as poly(methyl vinyl ether/maleic acid) (available commercially as Gantrez S-95, GAF Corporation, Wayne, N.J.) and a 2% aqueous solution of sodium chloride, with the resulting emulsion stabilized by adding two parts of polyoxyethylated (6) tridecyl alcohol (available as Emulphogene BC-610, GAF Corp.). Transfer sheets are formed by spreading a 0.002 to 0.004 inch thick layer of the composition on a release liner, covering the exposed side with a second release liner and drying at 150 degrees F. for 15 minutes. The resulting adhesive has approximately 0.7% electrolyte concentration by weight and demonstrates typical impedance values to dry skin of 130 k$\Omega$ at 10 Hz, self impedance values of 2 k$\Omega$ at 10 Hz and excellent adhesive tack to skin.

As shown in FIG. 1b, the lead side of electrode pad 1 is coated with a non-conducting pressure sensitive adhesive 4 on all of the surface of conductive substrate 2 except for an area large enough to allow an electrical contact access to conductive substrate 2. Although FIG. 1b depicts a central aperture in adhesive 4, other types of coatings are contemplated, such as parallel strips of adhesive with a central portion of the adhesive 4 surface left uncoated, etc. Adhesive 4 allows a removable adhesion to electrical contact housing 8 by presenting sufficient tack while leaving no adhesive residue after removal of the contact. An example of a suitable removable non-conductive adhesive is Type AS-23 acrylic based adhesive, manufactured by Adhesives Research, Inc.

In the preferred embodiment of the electrode pad shown in FIG. 1c, conductive substrate 2 is coated on both sides with conductive adhesives. Both the skin side adhesive 3 and conductive substrate 2 remain as described previously, while the lead side adhesive 5 is a removable adhesive that leaves no residue on the connector. It is preferred that the conductivity of adhesive 5 be obtained by loading an adhesive with the same materials as used to promote conductivity in conductive substrate 2 to obtain a non-polarizable electrode interface. The amount of loading necessary to obtain suitable conductivity does not reduce the tack of the adhesive below that needed for adequate adhesion to the connector, and adhesive 5 must be capable of meeting the electrical requirements given above for conductive substrate 2. In order to protect the adhesives during storage, release liners 3a and 5a in FIG. 1c cover the electrode pad.

Many suitable adhesives for making lead side adhesive 5 are available and are known to those skilled in the adhesive art. Acceptable adhesive bases include, but are not limited to, the adhesive bases listed above for adhesive 3. An example of an acceptable adhesive based on vinyl ether polymers can be made by mixing equal parts of poly(methyl vinyl ether) polymer (such as Gantrez S-95, as above) and water. The resulting mixture is stabilized by adding two pats of polyoxyethylated (6) tridecyl alcohol (emulphogene BC-610 as above); the conductive loading materials are mixed into the resulting composition, which may be spread on release liners and dried at 150 degrees F. to make transfer adhesive sheets for lamination to conductive substrate 2.

Figure 2A:
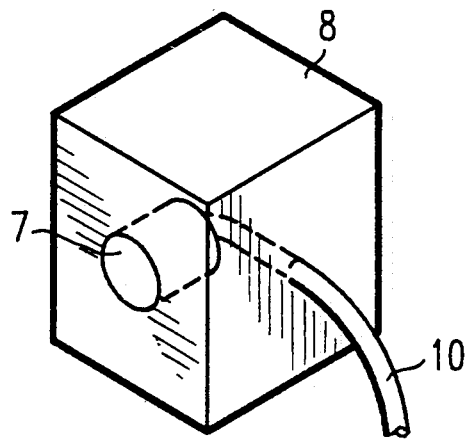
FIGS. 2a and 2b are perspective views of the pad connectors of the invention.
Figure 2B:
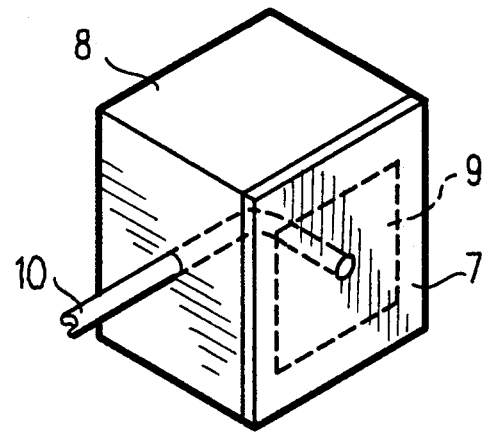

Electrical connectors for electrode pad 1 are shown in FIGS. 2a and 2b. In FIG. 2a, conductive electrical contact 7, extending about 0.125 inches from the face of insulative housing 8, is composed of the same material, for example silver and silver chloride powders or zinc and zinc sulfate powders or a mixture of titanium hydride, silver chloride, sodium tungsten dihydride and graphite powders, as is loaded into conductive substrate 2 for achieving a non-polarizable electrode interface, and is press molded to form a solid piece. Alternatively, a polymeric material such as silicone rubber or polytetrafluoroethylene or plasticized polyvinylchloride (PVC) or other such material loaded with the same non-polarizing powders as in substrate 2 may be used for contact 7, but only if it results in a material that meets the electrical requirements outlined above for conductive substrate 2. Housing 8 contains an electrical preamp as shown in my U.S. Pat. Nos. 4,669,479, 4,751,471 and 4,763,659, or passive lead wire 10 connected to contact 7, thus isolating any metallic components from contact with physiological fluids. Housing 8 also presents a surface for releasable adhesion to electrode pad 1. Suitable materials for housing 8 include silicone rubber and polypropylene. In FIG. 2b, electrical contact 7 is enlarged to include most if not all of the mating surface of the connector, and may be composed of a press molded plate of the same powders as are loaded into substrate 2 for achieving a non-polarizable electrode interface, or preferably silicone rubber or plasticized PVC or polytetrafluoroethylene loaded with the same non-polarizing powders as in substrate 2. Loaded silicone rubber is preferred for its releasable surface characteristics. Housing 8 is any moldable insulative material, and seals a passive lead wire 10 connected to contact 7 from exposure to fluids. A sheet of metallic screening or foil 9 embedded in contact 7 or laminated to the backside of contact 7 and in physical contact with lead wire 10 may used to improve the conductivity of the lead wire connection to contact 7.

The above described electrode pad and connector have several advantages. An electrically stable, non-polarizable electrode has been realized in a configuration that is simple and inexpensive to manufacture, easy to use without need for skin prepping or wet creams, is conformable and non-irritating to skin, and maintains electrical stability even in the presence of excessive quantities of physiological saline fluids flooding over the top of the electrode and completely soaking the pad and connector.

Obviously, numerous modifications and variations of the present invention are possible in light of the above teachings. It is therefore to be understood that within the scope of the appended claims, the invention may be practiced otherwise than as specifically described herein.

What is claimed is:

1. A dry electrode system for the detection of biopotentials existing on the surface of the skin of a living body, comprising:
   a dry electrode having opposed sides, one of which is adapted to contact said skin, said dry electrode comprising a non-polarizable conductive substrate having opposed sides, and first and second adhesive layers applied to the opposite sides of said non-polarizable conductive substrate, said first adhesive layer being ionically conductive and adapted to adhere said dry electrode to said skin; and
   a non-polarizable electrically conductive contact adhered to by said second adhesive layer and in conductive contact with said substrate via said second adhesive layer for conducting a biopotential from said dry electrode.

2. A dry electrode system according to claim 1, wherein said conductive substrate includes a base material selected from the group consisting of silicone rubber, plasticized polyvinylchloride, polyurethane foam and polytetrafluoroethylene.

3. A dry electrode system according to claim 1, wherein said conductive substrate is resilient and has a rebound value of not less than 5%.

4. A dry electrode system according to claim 3, wherein said resilient conductive substrate comprises a base material selected from the group consisting of an cell foam, a polyurethane foam, a closed cell foam, and a cross linked vinyl nitrite polymer.

5. A dry electrode system according to claims 2 or 4, wherein said base material of said conductive substrate is impregnated with silver and silver chloride powders, or zinc and zinc sulfate powders, or a mixture of titanium hydride, silver chloride, sodium tungstate dihydride and graphite powders, in sufficient quantity to establish a 10 Hz impedance of not more than 1500 ohms to a 1.5% sodium chloride solution.

6. A dry electrode system according to claims 1, 2, 3 or 4, wherein said first adhesive layer comprises an adhesive base selected from the group consisting of polyvinylpyrrolidone, polyvinylpyridine, vinyl ether polymers and cellulose derivatives.

7. A dry electrode system according to claim 6, wherein said first adhesive layer includes and thereby derives ionic conductivity from dissolved chloride ions of 0.15% to 1.5% concentration by weight of said first adhesive layer.

8. A dry electrode system according to claim 5, wherein said first adhesive layer comprises an adhesive base selected from the group consisting of polyvinylpyrrolidone, polyvinylpyrridine, vinyl ether polymers and cellulose derivatives.

9. A dry electrode system according to claim 8, wherein said first adhesive layer includes and thereby derives ionic conductivity from dissolved chloride ions of 0.15% to 1.5% concentration by weight of said first adhesive layer.

10. A dry electrode system according to claim 9, wherein said second adhesive layer comprises an electrically insulative material partially coating the surface of a portion of said conductive substrate.

11. A dry electrode system according to claim 9, wherein said second adhesive layer comprises an adhesive base selected from the group consisting of polyvinylpyrrolidone, polyvinylpyridine, vinyl ether polymers and cellulose derivatives.

12. A dry electrode system according to claim 11, wherein said adhesive base of said second adhesive layer is impregnated with silver and silver chloride powders, or zinc and zinc sulfate powders or a mixture of titanium hydride, silver chloride, sodium tungstate dihydride and graphite powders, in sufficient quantity to establish a 10 Hz impedance of not more than 1500 ohms to a 1.5% sodium chloride solution.

13. A dry electrode system according to claim 12, wherein said conductive contact comprises a material including silver and silver chloride powders, or zinc and zinc sulfate powders, or a mixture of titanium hydride, silver chloride, sodium tungstate dihydride and graphite powders, in sufficient quantity to establish a 10 Hz impedance of not more than 1500 ohms to a 1.5% sodium chloride solution.

14. A dry electrode system according to claim 13, wherein said conductive contact further comprises silicone rubber, plasticized polyvinylchloride or polyetrafluroethylene.

15. A dry electrode system according to claim 1, further comprising:
   a water insoluble adhesive adapted to adhere to skin partially coated on said first adhesive layer.

16. A dry electrode system according to claim 1, wherein said second adhesive layer comprises an electrically insulative material partially coating the surface of a portion of said conductive substrate.

17. A dry electrode system according to claim 1, wherein said second adhesive layer comprises an adhesive base selected from the group consisting of polyvinylpyrrolidone, polyvinylpyridine, vinyl ether polymers and cellulose derivatives.

18. A dry electrode system according to claim 17, wherein said adhesive base of second adhesive layer is impregnated with silver and silver chloride powders, or zinc and zinc sulfate powders or a mixture of titanium hydride, silver chloride, sodium tungstate dihydride and graphite powders, in sufficient quantity to establish a 10 Hz impedance of not more than 1500 ohms to a 1.5% sodium chloride solution.

19. A dry electrode system according to claim 1, wherein said conductive contact comprises a material including silver and silver chloride powders, or zinc and zinc sulfate powders, or a mixture of titanium hydride, silver chloride, sodium tungstate dihydride and graphite powders, in sufficient quantity to establish a 10 Hz impedance of not more than 1500 ohms to a 1.5% sodium chloride solution.

20. A dry electrode system according to claim 19, wherein said conductive contact further comprises silicone rubber, plasticized polyvinylchloride or polytetrafluoroethylene.

21. A dry electrode for enabling electrical and mechanical connection between the skin of a living body and an electrically conductive contact, comprising:
   a non-polarizable conductive substrate having opposed sides; and
   first and second adhesive layers applied to the opposed sides of said non-polarizable conductive substrate, said first adhesive layer being ionically conductive and adapted to adhere said substrate to said skin, said second adhesive layer adapted to adhere said substrate to said contact.

22. A dry electrode according to claim 21, wherein said conductive substrate includes a base material selected from the group consisting of silicone rubber, plasticized polyvinylchloride, polyurethane foam and polytetrafluoroethylene.

23. A dry electrode according to claim 21, wherein said conductive substrate is resilient and has a rebound value of not less than 5%.

24. A dry electrode according to claim 23, wherein said resilient conductive substrate comprises a base material selected from the group consisting of an open cell foam, a polyurethane foam, a closed cell foam, and a cross linked vinyl nitrite polymer.

25. A dry electrode according to claims 22 or 24, wherein said base material of said conductive substrate is impregnated with silver and silver chloride powders, or zinc and zinc sulfate powders, or a mixture of titanium hydride, silver chloride, sodium tungstate dihydride and graphite powders, in sufficient quantity to establish a 10 Hz impedance of not more than 1500 ohms to a 1.5% sodium chloride solution.

26. A dry electrode according to claims 21, 22, 23 or 24, wherein said first adhesive layer comprises an adhesive base selected from the group consisting of polyvinylpyrrolidone, polyvinylpyrridine, vinyl ether polymers and cellulose derivatives.

27. A dry electrode according to claim 26, wherein said first adhesive layer includes and thereby derives ionic conductivity from dissolved chloride ions of 0.15% to 1.5% concentration by weight of said first adhesive layer.

28. A dry electrode according to claim 25, wherein said first adhesive layer comprises an adhesive base selected from the group consisting of polyvinylpyrrolidone, polyvinylpyrridine, vinyl ether polymers and cellulose derivatives.

29. A dry electrode according to claim 28, wherein said first adhesive layer includes and thereby derives ionic conductivity from dissolved chloride ions of 0.15% to 1.5% concentration by weight of said first adhesive layer.

30. A dry electrode according to claim 29, wherein said second adhesive layer comprises an electrically insulative material partially coating the surface of a portion of said conductive substrate.

31. A dry electrode according to claim 29, wherein said second adhesive layer comprises an adhesive base selected from the group consisting of polyvinylpyrrolidone, polyvinylpyridine, vinyl ether polymers and cellulose derivatives.

32. A dry electrode accordign to claim 31, wherein said adhesive base of said second adhesive layer is impregnated with silver and silver chloride powders, or zinc and zinc sulfate powders or a mixture of titanium hydride, silver chloride, sodium tungstate dihydride and graphite powders, in sufficient quantity to establish a 10 Hz impedance of not more than 1500 ohms to a 1.5% sodium chloride solution.

33. A dry electrode according to claim 21, further comprising:
   a water insoluble adhesive adapted to adhere to skin partially coated on said first adhesive layer.

34. A dry electrode according to claim 21, wherein said second adhesive layer comprises an electrically insulative material partially coating the surface of a portion of said conductive substrate.

35. A dry electrode according to claim 21, wherein said second adhesive layer comprises an adhesive base selected from the group consisting of polyvinylpyrrolidone, polyvinylpyridine, vinyl ether polymers and cellulos derivatives.

36. A dry electrode according to claim 35, wherein said adhesive base of said second adhesive layer is impregnated with silver and silver chloride powders, or zinc and zinc sulfate powders or a mixture of titanium hydride, silver chloride, sodium tungstate dihydride and graphite powders, in sufficient quantity to establish a 10 Hz impedance of not more than 1500 ohms to a 1.5% sodium chloride solution.

* * * * *